(12) United States Patent
Sikkema et al.

(10) Patent No.: US 8,299,202 B2
(45) Date of Patent: Oct. 30, 2012

(54) PHENOL COMPOUNDS AND (CO)POLYMERS THEREOF

(75) Inventors: Doetze Jakob Sikkema, Wageningen (NL); Ronny Mathieu Versteegen, Hegelsom (NL); Maarten Jozef Pouderoijen, Nijmegen (NL)

(73) Assignee: Doetze Jakob SIKKEMA, Wageningen (NL)

( * ) Notice: Subject to any disclaimer, the term of this patent is extended or adjusted under 35 U.S.C. 154(b) by 0 days.

(21) Appl. No.: 12/865,067

(22) PCT Filed: Jan. 30, 2009

(86) PCT No.: PCT/NL2009/050042
§ 371 (c)(1),
(2), (4) Date: Nov. 5, 2010

(87) PCT Pub. No.: WO2009/096786
PCT Pub. Date: Aug. 6, 2009

(65) Prior Publication Data
US 2011/0039958 A1 Feb. 17, 2011

Related U.S. Application Data

(60) Provisional application No. 61/024,612, filed on Jan. 30, 2009.

(51) Int. Cl.
*C08G 61/02* (2006.01)

(52) U.S. Cl. .......... 528/86; 528/168; 528/172; 528/211; 528/423; 525/390; 427/385.5; 429/12

(58) Field of Classification Search .............. 528/86, 528/168, 172, 211, 423; 525/390; 427/385.5; 429/12
See application file for complete search history.

(56) References Cited

U.S. PATENT DOCUMENTS

| | | | |
|---|---|---|---|
| 5,525,436 A | 6/1996 | Savinell et al. | |
| 5,716,727 A | 2/1998 | Savinell et al. | |
| 6,025,085 A | 2/2000 | Savinell et al. | |
| 6,723,757 B1 | 4/2004 | Kerres et al. | |
| 7,045,241 B2 | 5/2006 | Akita et al. | |
| 7,235,320 B2 | 6/2007 | Calundann et al. | |
| 2004/0116425 A1 | 6/2004 | Li et al. | |
| 2006/0057449 A1 | 3/2006 | Calndann et al. | |
| 2007/0141426 A1 | 6/2007 | Choi et al. | |
| 2008/0113227 A1* | 5/2008 | Geormezi et al. | 429/12 |
| 2008/0248364 A1* | 10/2008 | Gourdoupi et al. | 429/33 |

FOREIGN PATENT DOCUMENTS

| | | |
|---|---|---|
| EP | 1 760 110 A1 | 3/2007 |
| WO | WO 02/081547 A1 | 10/2002 |
| WO | WO 2005/095469 A1 | 10/2005 |

OTHER PUBLICATIONS

Yu et al., "Conformationally Driven Asymmetric Induction of a Catalytic Dendrimer," *J. Am. Chem. Soc.*, vol. 130, pp. 7845-7847 (2008).

Davies et al., "Use of Suzuki Cross-Coupling as a Route to 2-phenoxy-6-iminopyridines and Chiral 2-phenoxy-6-(methanamino)pyridines," *Tetrahedron*, vol. 64, pp. 9857-9864 (2008).

Beyer et al., "Uber die Michael-Additional von Picolyl-(2)-Ketonen," *Chemische Berichte*, vol. 90, pp. 592-598 (1957).

Chardonnens et al., "Sur les derives de la fluorenone," *Helvetia Chimica ACTA*, vol. 3, No. 62, pp. 657-666 (1979).

Eichinger et al., "Neue Synthesen alkylaryl- und diaryl-disubstituierter Phenole und Salicylsaure-ethylester," *Synthesis*, vol. 12, pp. 1061-1064 (1987).

Wang et al., "Synthesis, X-ray Structure, and Self-Assembly of Functionalized Bis(2,2':6',2"—terpyridinyl)arenes," *Org. Lett.*, vol. 6, No. 8, pp. 1197-1200 (2004).

Champouret et al., "Sterically Variable Dizine Complexes Bearing bis(iminopyridyl)phenolate ligands: synthesis, structures and reactivity studies," *Dalton Transactions*, vol. 40, pp. 4565-4575 (2007).

Wang et al., Synthesis of a Water-Soluble Hexameric Metallomacrocycle and its Oxidized single-wall carbon nanotube composite, *Journal of Materials Chem.*, vol. 17, No. 29, pp. 3023-3029 (2007).

International Search Report for PCT/NL2009/050042 filed May 28, 2009.

Hara et al. JMS-Rev. Macromol. Chem. Phys., C34(3), 1994 pp. 325-373.

Handbook of Chemistry and Physics, 66th ed. (1985-1986) (Groups 6-12), CRC Press, Inc., Boca Raton, Florida.

Samms, et al., "Thermal Stability of Proton Conducting Acid Doped Polybenzimidazole in Simulated Fuel Cell Environments," J. Electrochem. Soc. vol. 143, No. 4, Apr. 1996, 1225-1232.

Wang et al, "A direct methanol fuel cell using acid-doped Polybenzimidazole as polymer electrolyte," J. Appl. Electrochemistry, vol. 26, 1996, p. 751-756.

* cited by examiner

*Primary Examiner* — Shane Fang
(74) *Attorney, Agent, or Firm* — Gilberto M. Villacorta; Sunit Talapatra; Foley & Lardner LLP

(57) ABSTRACT

The present invention relates to A phenol compound according to Formula (I): wherein: $R^1$ is selected from the group consisting of, optionally substituted, 2-pyridyl, 3-pyridiyl and 4-pyridyl groups, wherein $R^1$ is at position 2 or 3 of the phenol ring; $R^2$ is selected from the group consisting of, optionally substituted, 2-pyridyl, 3-pyridiyl, 4-pyridyl and phenyl groups, wherein $R^2$ is at position 5 or 6 of the phenol ring; and the phenol ring is optionally substituted at one or two positions, independently selected from positions 2, 3, 5 and 6, with a halogen atom or a with an optionally substituted $C_6$-$C_{12}$ aryl group or an optionally substituted $C_1$-$C_{10}$ alkyl group. The present invention relates also to (co)polymers comprising the phenol compound according to Formula (I) and membranes and ionic resins comprising said (co)polymers.

(I)

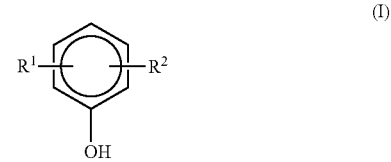

20 Claims, No Drawings

PHENOL COMPOUNDS AND (CO)POLYMERS THEREOF

CROSS-REFERENCE TO RELATED APPLICATION(S)

This application is a National Phase of PCT/NL2009/050042, filed Jan. 30, 2009, which claims priority from U.S. Provisional Patent Application No. 61/024,612, filed on Jan. 30, 2008. The contents of these applications are incorporated herein by reference in their entirety.

FIELD OF THE INVENTION

The present invention relates to novel monomers, (co)polymers prepared from these novel monomers, a process for the preparation of such (co)copolymers and the application of such polymers in membranes having a well-defined selectivity and an improved resistance to harsh environments.

BACKGROUND OF THE INVENTION

In the art, there is still a need for polymer membranes having a well-defined selectivity and an improved resistance to harsh environments. Many separation processes would benefit from the option of being performed at higher temperatures than is currently feasible with state-of-the-art polymer membranes. In particular, anion exchange materials which are often based on polyethylenimine or on trimethylammonium derivatives of polystyrene have limited thermo-oxidative stability.

Highly thermo-oxidatively stable Brønsted basic membranes, after complexation with a strong acid, are also of great potential value in polymer membrane fuel cells. Such higher operating temperatures may lead to simpler fuel cell stack design and allow the use of less pure hydrogen as well as other fuels compared to Nafion®-based fuel cells. Nafion® perfluorosulfonic acid ionomers have the general structure (Butler, G. B.; O'Driscoll, K. F.; Wilkes, G. L. *JMS-Rev. Macromol. Chem. Phys.* 1994, C34(3), 325-373):

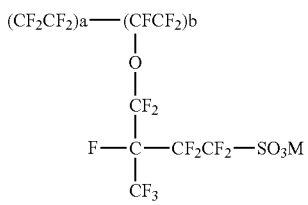

Another disadvantage of Nafion® membranes is that it requires 100% water saturation (i.e. a 100% RH environment) to achieve the required conductivity since water is the proton conducting phase. Hence, operation above 100° C. is virtually impossible due to the water loss from the Nafion® membranes, although an improved performance is expected at higher operating temperatures, e.g. a temperature in the range of about 120° C. up to about 150° C. Hybrid Nafion® membranes are also known in the art but have been applied without much success.

U.S. Pat. Nos. 5,525,436, 5,716,727 and 6,025,085 to R. F. Savinell and Morton H. Litt, incorporated by reference herein, disclose PBI ("PBI" means polybenzimidazole) and similar polymers doped with phosphoric acid. See also J-T Wang, J. S. Wainright, R. F. Savinell and M. H. Litt, J. Appl. Electrochem. 26, 751, 1996 and S. R. Samms, R. Wasmus and R. F. Savinell, J. Electrochem. Soc. 143, 1225, 1996. However, these systems have the disadvantage that they loose phosphoric acid during prolonged use which is presumably related to coagulation of the PBI by water from its phosphoric acid complex (cf. e.g. U.S. Pat. No. 7,045,241 to Akita Hiroshi and Komiya Teruaki, incorporated by reference herein, which discloses the isolation of a PBI composition by pouring its solution in polyphosphoric acid into water).

U.S. Pat. No. 6,723,757 to J. Kerres, A. Ullrich and T. Haring, incorporated by reference, discloses acid-base polymer blend membranes comprising as a first component either a cation exchanging polymer or an anion exchanging polymer and as a second component a polymer comprising one or more nitrogen containing basis moieties. However, pyridine as a nitrogen basic moiety is not disclosed.

U.S. Pat. No. 7,235,320 to G. Calundann, M. J. Sansone, O. Uensal and J. Kiefer, incorporated by reference, discloses a polymer membrane based on polyazoles wherein the azole moiety may be a pyridinylene moiety (structures XVI and XVII).

US 2006/0057449, also to G. Calundann, M. J. Sansone, O. Uensal and J. Kiefer, incorporated by reference, discloses a polymer membrane based on sulphonated polymers comprising recurring benzimidazole units.

US 2007/0141426 to S-w. Choi, H-y Sun, M-j Lee and W-s Jeon, incorporated by reference, discloses systems obtained by crosslinking polybenzimidazole with a benzoxazine-based monomer, wherein the nitrogen atom may be substituted with a 2-pyridyl or 3-pyridyl group.

There is, however, still a need in the art for improved polymer membranes.

SUMMARY OF THE INVENTION

The present invention relates to a phenol compound according to Formula (I):

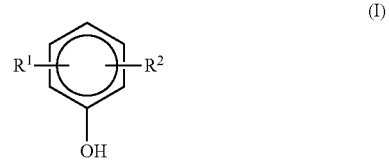

wherein:
$R^1$ is selected from the group consisting of, optionally substituted, 2-pyridyl, 3-pyridiyl and 4-pyridyl groups, wherein $R^1$ is at position 2 or 3 of the phenol ring;
$R^2$ is selected from the group consisting of, optionally substituted, 2-pyridyl, 3-pyridiyl, 4-pyridyl and phenyl groups, wherein $R^2$ is at position 5 or 6 of the phenol ring; and
the phenol ring is optionally substituted at one or two positions, independently selected from positions 2, 3, 5 and 6, with a halogen atom or a with an optionally substituted $C_6$-$C_{12}$ group or an optionally substituted $C_1$-$C_{10}$ alkyl group.

The present invention also relates to (co)polymers made of the phenol compound according to Formula (I) and membranes and ionic resins comprising such (co)polymers.

DETAILED DESCRIPTION OF THE INVENTION

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the element are present, unless the context clearly requires that there is one and only one of the elements. The indefinite article "a" or "an" thus usually means "at least one".

According to the present invention, suitable substituents for alkyl groups, aryl groups, phenyl groups and aryl groups include halogen atoms, in particular fluorine, chlorine and bromine atoms, and $C_1$-$C_6$ alkyl groups, wherein the alkyl groups may be linear or branched.

According to the present invention, it is preferred that $R^2$ is selected from the group consisting of, optionally substituted, 2-pyridyl, 3-pyridiyl, 4-pyridyl groups. Suitable substituents include halogen atoms, in particular halogen atoms selected from the group consisting of fluorine, chlorine and bromine atoms, and optionally substituted $C_6$-$C_{12}$ aryloxy groups. According to the present invention, it is preferred that $R^1$ and $R^2$ are an optionally substituted 3-pyridyl group.

It is also preferred that $R^1$ is at position 2 of the phenyl ring.

It is furthermore preferred that $R^2$ is at position 6 of the phenyl ring.

The present invention also relates to homopolymers or copolymers (further referred to as (co)polymers) which comprises a phenol compound according to the present invention. When the polymer is a copolymer, suitable comonomers include optionally substituted phenol monomers. Suitable substituents for such optionally substituted phenol monomers include halogen atoms, in particular halogen atoms selected from the group consisting of fluorine, chlorine and bromine atoms, optionally substituted $C_6$-$C_{12}$ aryl groups and optionally substituted $C_1$-$C_{10}$ alkyl groups. The alkyl groups may further be linear or branched, but are preferably not α-branched. The alkyl group may also comprise a cyclic system, provided it comprises at least 3 carbon atoms.

More in particular, the present invention relates to a copolymer according to Formula (II):

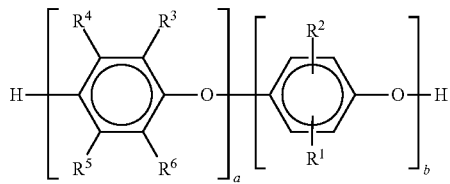

wherein:
$R^1$ is selected from the group consisting of, optionally substituted, 2-pyridyl, 3-pyridiyl and 4-pyridyl groups, wherein $R^1$ is at position 2 or 3 of the phenol ring;
$R^2$ is selected from the group consisting of, optionally substituted, 2-pyridyl, 3-pyridiyl, 4-pyridyl and phenyl groups, wherein $R^2$ is at position 5 or 6 of the phenol ring; the phenol ring bearing $R^1$ and $R^2$ is optionally substituted at one or two positions, independently selected from positions 2, 3, 5 and 6, with a halogen atom, with an optionally substituted $C_6$-$C_{12}$ aryl group or a with an optionally substituted $C_1$-$C_{10}$ alkyl group; and
one or two substituents selected from the group consisting of $R^3$, $R^4$, $R^5$ and $R^6$ are an, optionally substituted phenyl group, whereas the other substituents selected from the group consisting of $R^3$, $R^4$, $R^5$ and $R^6$ are selected from the group of hydrogen, halogen and optionally substituted $C_1$-$C_{10}$ alkyl groups.

According to the present invention, it is preferred that $R^2$ is selected from the group consisting of, optionally substituted, 2-pyridyl, 3-pyridiyl, 4-pyridyl groups.

It is furthermore preferred that $R^1$ and $R^2$ are an optionally substituted 2-pyridyl group.

It is also preferred according to the present invention that $R^1$ and $R^2$ are an optionally substituted 3-pyridyl group.

Additionally, in the copolymer according to Formula (II), $R^1$ is preferably at position 2 of the phenyl ring.

It is also preferred that $R^2$ is at position 6 of the phenyl ring.

Preferably, $R^3$ and $R^6$ are independently selected from the group of optionally substituted phenyl groups. Suitable substituents for the phenyl groups are fluorine and chlorine.

It is also preferred that in the copolymer according to Formula (II) that $R^4$ and $R^5$ are selected from the group of hydrogen, halogen, optionally substituted $C_6$-$C_{12}$ aryl and optionally substituted $C_1$-$C_{10}$ alkyl groups. As described above, the alkyl groups may be substituted with one or more halogen atoms, in particular halogen atoms selected from the group consisting of fluorine, chlorine and bromine atoms. The alkyl groups may further be linear or branched, but are preferably not α-branched. The alkyl group may also comprise a cyclic group, provided it comprises at least 3 carbon atoms.

The (co)polymers according to the present invention have generally a number average molecular weight $M_n$ of about 7,000 to about 300,000 and a weight average molecular weight $M_w$ of about 15,000 to about 1,000,000.

The present invention further relates to a process for polymerising a phenol compound according to Formula (I), wherein the phenol compound, optionally in the presence of a comonomer, is polymerised in the presence of a catalyst. According to the invention, it is preferred that the polymerisation is conducted in a solvent comprising a pyridine compound. More preferably, the solvent is a pyridine compound, in particular 3-chloropyridine.

According to the process of the present invention, it is preferred that the comonomer has the Formula (III):

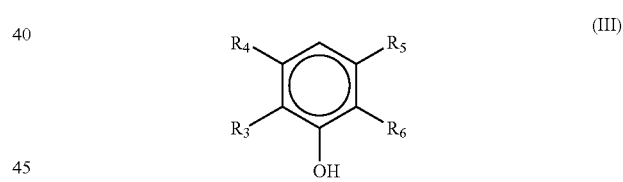

wherein one or two substituents selected from the group consisting of $R^3$, $R^4$, $R^5$ and $R^6$ are an, optionally substituted phenyl group, whereas the other substituents selected from the group consisting of $R^3$, $R^4$, $R^5$ and $R^6$ are selected from the group of hydrogen, halogen, optionally substituted $C_6$-$C_{12}$ aryl groups and optionally substituted $C_1$-$C_{10}$ alkyl groups. As described above, the alkyl groups may be substituted with one or more halogen atoms, in particular halogen atoms selected from the group consisting of fluorine, chlorine and bromine atoms. The alkyl groups may further be linear or branched, but are preferably not α-branched. The alkyl group may also comprise a cyclic group, provided it comprises at least 3 carbon atoms.

The catalyst employed in the process according to the present invention preferably comprises a metal, preferably a metal from Group 6-12 of the Periodic Table of Elements (IUPAC version 22 June 2007 and Handbook of Chemistry & Physics 66th Ed., 1985-1986; formerly Groups 6b-2b, cf. Handbook of Chemistry & Physics, 59th 9 Ed., 1978-1979). Most preferably, the catalyst comprises copper, preferably having an oxidation state of at least 1+. Obviously, the catalyst may comprise copper species having different oxidation states.

The (co)polymer according to the present invention is preferably used for the manufacture of membranes, in particular membranes for fuel cells, and ion exchange resins.

EXAMPLES

Example 1

Synthesis of 2,6-bis(3-pyridyl)phenol and its Polymerization 2,6-dibromophenyl benzyl ether

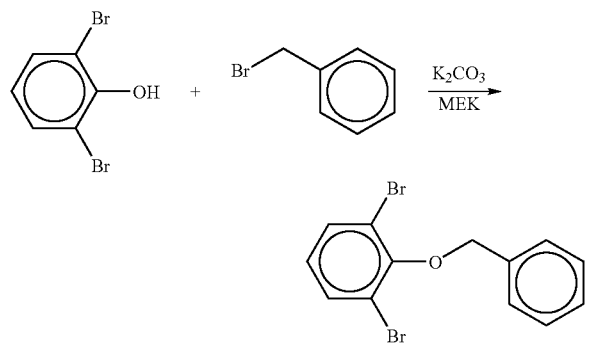

2,6-Dibromophenol (29.30 g, 116 mmol) and benzyl bromide (33.14 g, 194 mmol) were dissolved in 2-butanone (300 mL). Potassium carbonate (29.47 g, 213 mmol) was added, and the mixture was stirred for 1.5 hr at reflux temperature. The reaction mixture was cooled to room temperature, filtered, and evaporated to dryness. The remaining viscous oil was subjected to silicagel column chromatography, flushing with n-pentane to remove benzyl bromide, then DCM/n-pentane=1:1 to elute the product, yielding the product as a white crystalline solid (39.32 g, 99%). $^1$H-NMR (CDCl$_3$): δ=7.61 (dd, 2H), 7.54 (d, 2H), 7.41 (m, 3H), 6.90 (t, 1H), 5.04, (s, 2H) ppm.

2,6-bis(3-pyridyl)phenyl benzyl ether

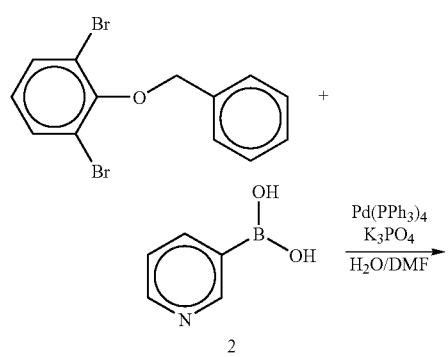

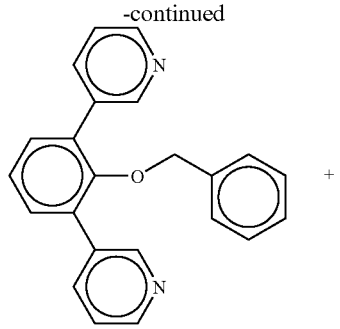

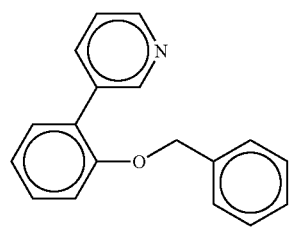

2,6-Dibromophenyl benzyl ether (25.61 g, 74.88 mmol), 3-pyridylboronicacid (20.25 g, 164.7 mmol), aqueous potassium carbonate (233 mL 2 M), and DMF (370 mL) were put together in a 1 liter flask. Oxygen was removed by several vacuum-argon cycles. Then Pd(PPh$_3$)$_4$ (5.38 g, 4.65 mmol) was added and the mixture was heated to 85° C. under an argon atmosphere. After 48 hr, the reaction mixture was cooled to rt, and poured into an ice/water mixture (1 L). This was extracted with diisopropylether (3 times 300 mL), and the combined organic layers were dried over MgSO$_4$, filtered, and the solvent was removed in vacuo, yielding a yellow crystalline solid. Recrystallisation from diethyl ether yielded the product as a white crystalline solid (10.34 g, 41%). The residue was further purified by column chromatography (silicagel, EtOAc/n-pentane=3:2), yielding another 2.60 g (10%) of the product (total yield 51%). $^1$H-NMR(CDCl$_3$):δ=8.80 (s, 2H), 8.59 (d, 2H), 7.93 (dd, 2H), 7.65 (d, 2H), 7.34 (m, 3H), 7.19 (t, 1H), 7.10 (t, 2H), 6.64 (d, 2H), 4.15 (s, 2H) ppm.

In another fraction of the column, the mono-substituted side-product was isolated as a white crystalline solid (6.07 g, 31%). $^1$H-NMR (CDCl$_3$):δ=8.81 (s, 1H), 8.57 (d, 1H), 7.89 (dd, 1H), 7.25-7.40 (m, 8H) 7.06 (t, 2H), 5.09 (s, 2H) ppm.

2,6-bis(3-pyridyl)phenol

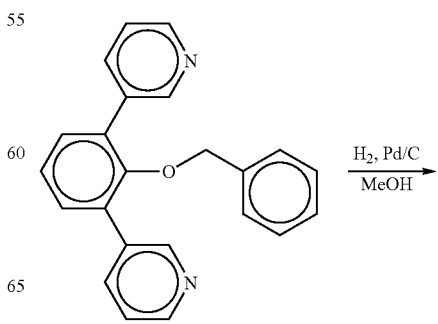

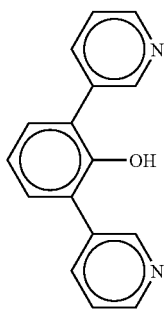

2,6-Bis(3-pyridyl)phenyl benzyl ether (16.70 g, 49.35 mmol) was dissolved in MeOH (200 mL). Argon was bubbled through this solution for 10 min to remove oxygen. Then Pd/C (500 mg 5 w %) was added, and the reaction mixture was put into the Parr-reactor and shaken for 16 hr under a hydrogen atmosphere at 80 psi. After the hydrogenation, the resulting precipitate was redissolved by heating to reflux. The hot mixture was filtered over diatomaceous earth, and the filter cake thoroughly washed with hot MeOH. Upon cooling to room temperature, the product crystallized as a white crystalline material (12.25 g, 99%). M.p.=211° C. $^1$H-NMR (DMSO):δ=8.74 (d, 2H), 8.55 (dd, 2H), 7.95 (dt, 2H), 7.48 (m, 2H), 7.34 (d, 2H), 7.11 (t, 1H).

Polymerization of 2,6-bis(3-pyridyl)phenol

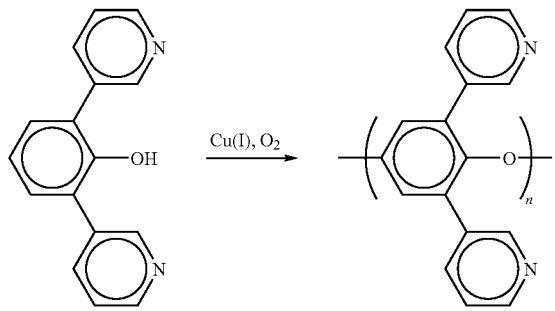

Cu(I)Cl (2.00 mg, 0.0202 mmol) and TMEDA (2.34 mg, 0.0202 mmol) were dissolved in 3-chloropyridine (2.5 mL). The mixture was heated to 85° C. and air was bubbled through for 10 min. Subsequently 2,6-bis(3-pyridyl)phenol (250 mg, 1.01 mmol) was added. The reaction mixture was heated for 16 hr at 85° C., while maintaining an air flow through the mixture. Then, it was cooled to room temperature and precipitated in diethyl ether (100 mL). The precipitate was washed thoroughly with diethyl ether, and dried in vacuo at 100° C. overnight. The polymer was obtained as a brown powder (220 mg, 88%). [η]=0.35 g/dl (0.1 w % in 95% $H_2SO_4$).

Example 2

2-(3-pyridyl)phenol

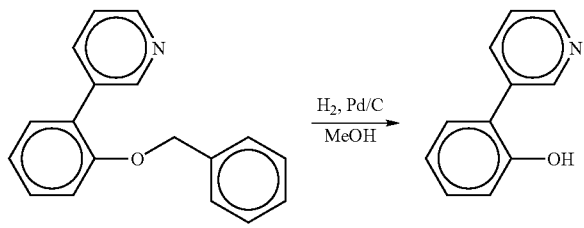

2-(3-pyridyl)phenyl benzyl ether (6.67 g, 25.52 mmol) was dissolved in MeOH (100 mL). Argon was bubbled through this solution for 10 min to remove oxygen. Then Pd/C (350 mg 5 w %) was added, and the reaction mixture was put into the Parr-reactor and shaken for 16 hr under a hydrogen atmosphere at 80 psi. After the hydrogenation, the mixture was filtered over diatomaceous earth, and the colourless solution was evaporated to dryness. The crude product was recrystallized from 2-propanol to yield a white crystalline material (3.54 g, 79%). M.p.=185° C. $^1$H-NMR (CDCl$_3$/MeOD): δ=8.76 (d, 1H), 8.43 (dd, 1H), 8.02 (dt, 1H), 7.39 (m, 1H), 7.21-7.29 (m, 2H), 6.95 (m, 2H).

The invention claimed is:

1. A polymer obtained by polymerizing a monomer according to Formula (I) and optionally one or more comonomers:

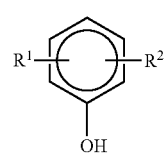

wherein:
R$^1$ is selected from the group consisting of optionally substituted, 2-pyridyl, 3-pyridyl and 4-pyridyl groups, wherein R$^1$ is at position 2 or 3 of the phenol ring;
R$^2$ is selected from the group consisting of, optionally substituted, 2-pyridyl, 3-pyridyl, 4-pyridyl and phenyl groups, wherein R$^2$ is at position 5 or 6 of the phenol ring; and
the phenol ring is optionally substituted at one or two positions, independently selected from positions 2, 3, 5 and 6, with a halogen atom or a with an optionally substituted C$_6$-C$_{12}$ aryl group or an optionally substituted C$_1$-C$_{10}$ alkyl group.

2. The polymer according to claim 1, wherein the polymer is a copolymer.

3. A copolymer according to Formula (II):

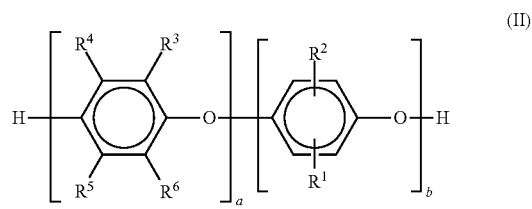

wherein:
a is 1 or more, b is 1 or more;
R$^1$ is selected from the group consisting of, optionally substituted, 2-pyridyl, 3-pyridyl and 4-pyridyl groups, wherein R$^1$ is at position 2 or 3 of the phenol ring;
R$^2$ is selected from the group consisting of, optionally substituted, 2-pyridyl, 3-pyridyl, 4-pyridyl and phenyl groups, wherein R$^2$ is at position 5 or 6 of the phenol ring;
the phenol ring bearing R$^1$ and R$^2$ is optionally substituted at one or two positions, independently selected from positions 2, 3, 5 and 6, with a halogen atom, with an optionally substituted C$_6$-C$_{12}$ aryl groups or with an C$_1$-C$_{10}$ alkyl group; and
one or two substituents selected from the group consisting of R$^3$, R$^4$, R$^5$ and R$^6$ are an, optionally substituted phenyl group, whereas the other substituents selected from the group R$^6$ consisting of R$^3$, R$^4$, R$^5$ and R$^6$ are selected from the group of hydrogen, halogen, optionally substituted $C_6$-$C_{12}$ aryl groups and optionally substituted $C_1$-$C_{10}$ alkyl groups.

4. The copolymer according to claim 3, wherein $R^2$ is selected from the group consisting of, optionally substituted, 2-pyridyl, 3-pyridyl, 4-pyridyl groups.

5. The copolymer according to claim 3, wherein $R^1$ and $R^2$ are an optionally substituted 2-pyridyl group.

6. The copolymer according to claim 3, wherein $R^1$ and $R^2$ are an optionally substituted 3-pyridyl group.

7. The copolymer according to claim 3, wherein $R^1$ is at position 2 of the phenyl ring.

8. The copolymer according to claim 3, wherein $R^2$ is at position 6 of the phenyl ring.

9. The copolymer according to claim 3, wherein $R^3$ and $R^6$ are independently selected from the group of optionally substituted phenyl groups.

10. The copolymer according to claim 3, wherein $R^4$ and $R^5$ are selected from the group of hydrogen, halogen, optionally substituted $C_6$-$C_{12}$ aryl groups and $C_1$-$C_{10}$ alkyl groups.

11. A process for preparing a polymer according to claim 1 comprising polymerizing a phenol compound according to Formula (I), optionally in the presence of a comonomer, in the presence of a catalyst.

12. The process according to claim 11, wherein the comonomer has the Formula (III):

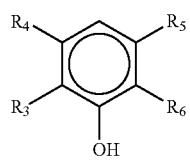

(III)

wherein one or two substituents selected from the group consisting of $R^3$, $R^4$, $R^5$ and $R^6$ are an, optionally substituted phenyl group, whereas the other substituents selected from the group consisting of $R^3$, $R^4$, $R^5$ and $R^6$ are selected from the group of hydrogen, halogen and optionally substituted aryl or $C_1$-$C_{10}$ alkyl groups.

13. The process according to claim 12, wherein the catalyst comprises copper.

14. The process according to claim 12, wherein the polymerisation is conducted in a solvent comprising a pyridine compound.

15. A membrane comprising the polymer according to claim 1.

16. A fuel cell comprising the membrane according to claim 15.

17. An ionic resin comprising the polymer according to claim 1.

18. The polymer of claim 1, wherein the polymer is a homopolymer.

19. The polymer of claim 18, wherein the homopolymer is represented by

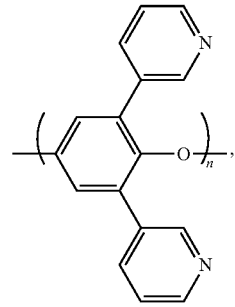

n is 2 or more.

20. The polymer of claim 2, wherein the copolymer comprises a phenol comonomer in addition to the monomer of Formula (I), wherein the phenol comonomer is optionally substituted with one or more substituents selected from the group consisting of halogen, optionally substituted $C_6$-$C_{12}$ aryl groups, and optionally substituted $C_1$-$C_{10}$ alkyl groups.

* * * * *

UNITED STATES PATENT AND TRADEMARK OFFICE
CERTIFICATE OF CORRECTION

PATENT NO. : 8,299,202 B2
APPLICATION NO. : 12/865067
DATED : October 30, 2012
INVENTOR(S) : Doetze Jakob Sikkema, Ronny Mathieu Versteegen and Maarten Jozef Pouderoijen It is certified that error appears in the above-identified patent and that said Letters Patent is hereby corrected as shown below:

Title page, Item (60) should read:

-- (60) Provisional application No. 61/024,612, filed on Jan. 30, 2008. --

Signed and Sealed this
Twelfth Day of February, 2013

Teresa Stanek Rea
*Acting Director of the United States Patent and Trademark Office*